United States Patent

Hsiao et al.

[11] Patent Number: 5,885,616
[45] Date of Patent: Mar. 23, 1999

[54] SUSTAINED RELEASE DRUG DELIVERY SYSTEM SUITABLE FOR ORAL ADMINISTRATION

[75] Inventors: John Hsiao, Livermore; I-Lan Sue, San Jose, both of Calif.

[73] Assignee: Impax Pharmaceuticals, Inc., Hayward, Calif.

[21] Appl. No.: 912,722

[22] Filed: Aug. 18, 1997

[51] Int. Cl.[6] ................................................. A61K 9/24
[52] U.S. Cl. ....................... 424/472; 424/461; 424/490; 424/494; 424/495; 424/497
[58] Field of Search ................... 424/472, 490, 424/495, 494, 497, 461

[56] References Cited

U.S. PATENT DOCUMENTS 4,894,240   1/1990   Geoghegan et al. .
5,320,853   6/1994   Noda et al. .
5,439,689   8/1995   Hendrickson et al. .
5,474,786   12/1995  Kotwal et al. .

OTHER PUBLICATIONS

{711} Dissolution; USP 23; Physical Tests {711} 1791–1794, 2185,3208–3209, 2577–2578, 3794–3495, 2833–2834.
{724} Drug Release; USP 23; Physical Tests 1793–1799, 2534–2536, 2709–2715, 3012–3017, 3209–3215, 3468–3474.

*Primary Examiner*—Thurman K. Page
*Assistant Examiner*—Brian K. Seidleck
*Attorney, Agent, or Firm*—Arter & Hadden, LLP

[57] ABSTRACT

A single bead drug delivery system suitable for oral administration with multiply layered drug and polymer compartments can provide a two-step release of active agent to facilitate an immediate yet sustained drug delivery over a 24 hour period following oral administration with minimized variance between peak and trough levels of therapeutic drug amounts.

20 Claims, 4 Drawing Sheets

SUSTAINED RELEASE DRUG DELIVERY SYSTEM SUITABLE FOR ORAL ADMINISTRATION

FIELD OF THE INVENTION

The present invention pertains to a drug delivery system suitable for oral administration that facilitates a two-step release of the active agent. A key aspect of the present invention is the discovery that a single orally administrable bead with multiply layered drug and polymer compartments can release the active agent in multiple phases to provide an immediate yet sustained drug delivery over a 24 hour period.

BACKGROUND OF THE INVENTION

Drug efficacy generally depends upon the ability of the drug to reach its target in sufficient quantity to maintain therapeutic levels for the desired time period. Orally administered drugs must overcome several obstacles to reach their desired targets. Before orally administered drugs enter the general circulation of the human body, they are absorbed into the capillaries and veins of the upper gastrointestinal tract and are transported by the portal vein to the liver. The pH and enzymatic activities found in gastrointestinal fluids may inactivate the drug or cause the drug to dissolve poorly. In addition, following their absorption in the intestine, orally administered drugs are often subject to a "first pass" clearance by the liver and excreted into bile or converted into pharmacologically inactive metabolites. Decreased bioavailability of orally administered drugs is a consequence of this first pass effect.

Orally administered drugs subject to the first pass effect generally exhibit non-linear pharmacokinetics. Until the liver's metabolic capacity has been exceeded, the amount of such drugs in the bloodstream is significantly lower than the amount administered. This metabolic elimination of the given dose results in reduced bioavailability. However, once the administered dose exceeds the liver's metabolic capacity, a significant increase in the drug concentration in the bloodstream may be obtained. The first pass phenomenon presents particular difficulties in the maintenance of therapeutic levels of an orally administered drug over an extended period such as 12 or 24 hours.

Drug delivery systems which have evolved with respect to orally administered drugs subject to the first pass effect include formulations capable of immediate drug release that are suitable for administration from 3–4 times daily, and formulations capable of immediate and sustained drug release that are suitable for once-daily administration. The second type of formulation is preferred because patient compliance with prescribed drug regimens involving once-daily administration is substantially higher than those involving multiple administrations. A sustained release formulation, however, may subject the patient to toxic drug levels over part of the dosing period and sub-therapeutic drug levels over other portions of the dosing period, if the drug release does not occur at appropriate time intervals. The maintenance of therapeutic levels of an orally administered drug over an extended period thus depends upon a drug delivery system capable of providing an appropriate release pattern.

Various drug delivery systems have been designed in attempts to ameliorate the first pass effect. U.S. Pat. No. 5,439,689 describes one such system designed to deliver the calcium antagonist diltiazem in a manner to maintain the drug in the bloodstream in therapeutic drug levels throughout the 24 hour period following oral administration. This formulation accomplishes its dosing profile through the use of a blend of immediate drug release beads and delayed drug release beads. One disadvantage of this system is the relatively complicated manufacturing scheme. In contrast to a formulation comprising the blend of two types of drug release beads, a single bead formulation could be manufactured more simply. A single bead formulation would not require the time and effort required by the separate production of two types of drug release beads to prepare a final dosage form. Moreover, concerns regarding blending or double-filling homogeneity would be eliminated.

U.S. Pat. No. 4,894,240 describes an extended release drug delivery system in a single bead formulation. This system was also designed to deliver diltiazem in therapeutic drug levels over a 24 hour period following oral administration. However, subsequent tests demonstrated that the commercial product based on this patent's teachings was unable to provide optimal diltiazem blood levels over the 24 hour period following oral administration because of significant variances between peak and trough levels.

A valuable contribution to the art therefore would be the development of a drug delivery system in a single bead formulation suitable for oral administration that facilitates an immediate yet sustained release of the active agent over the 24 hour period following oral administration while minimizing the variance between peak and trough levels.

SUMMARY OF THE INVENTION

Accordingly, an objective of the present invention is a single orally administrable bead with multiply layered drug and polymer compartments that can release the active agent in multiple phases to provide an immediate yet sustained drug delivery over a 24 hour period with minimal variance between peak and trough levels. Another objective of the present invention is the control of the lag time between the initial and subsequent release of active agent. One other objective of the present invention is a comparative increase in active agent load (and thus drug density) above that achievable through a single bead formulation having a single layer of active agent.

The present invention accomplishes these objectives through a drug delivery system suitable for oral administration having a first drug compartment containing an effective amount of an active agent, or a pharmaceutically acceptable salt thereof, optionally in association with pharmaceutically acceptable binder(s) or excipient(s); a first polymer compartment which substantially envelops the first drug compartment to form a first drug/polymer interface; a second drug compartment containing an effective amount of an active agent, or a pharmaceutically acceptable salt thereof, optionally in association with pharmaceutically acceptable binder(s) or excipient(s), where the second drug compartment substantially envelops the first polymer compartment to form a second drug/polymer interface; and a second polymer compartment which substantially envelops the second drug compartment to form a third drug/polymer interface.

The active agent contained in the second drug compartment facilitates an initial release of active agent in an amount sufficient to achieve therapeutic levels at the appropriate target. The lag time and release rate of active agent from the second drug compartment is predominantly controlled by the second polymer compartment, which is composed mainly of one or more water insoluble polymers, one or more pH sensitive (i.e., enteric) polymers, and/or one or more water soluble polymers. Accordingly, the character of the initial release phase may be altered by changing the polymer composition of the second polymer compartment.

Upon exposure of the drug delivery system to higher pHs, a pH sensitive polymer in the second polymer layer can dissolve. The dissolution of the pH sensitive polymer disrupts the polymer film and facilitates the complete release of the active agent from the second drug compartment. In turn, the first polymer compartment becomes exposed to the surrounding medium.

The active agent contained in the first drug compartment provides the sustained release of active agent in an amount sufficient to maintain therapeutic levels at the appropriate target throughout the 24 hour period following oral administration. When the second polymer and second drug compartments dissolve and/or detach from the drug delivery system, the first polymer compartment becomes exposed to the surrounding medium. The lag time and release rate of active agent from the first drug compartment is predominantly controlled by the first polymer compartment, which is composed mainly of one or more water insoluble polymers, one or more pH sensitive (i.e., enteric) polymers, and/or one or more water soluble polymers. Where a water soluble polymer is employed, the dissolution of the first polymer compartment facilitates the release of the active agent from the first drug compartment. Accordingly, the character of the sustained release phase may be altered by changing the polymer composition of the first polymer compartment.

DETAILED DESCRIPTION OF DRAWINGS

Figure 1:
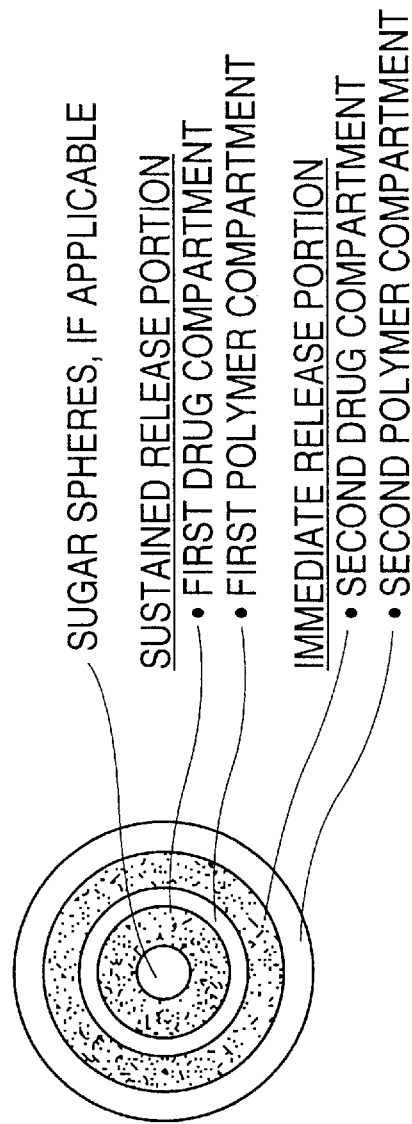

FIG. 1 is a schematic drawing depicting a typical bead containing multiple layers of active drug and polymer materials. The release of the active agent from the second drug compartment is predominantly controlled by the second polymer compartment and provides an immediate release of active agent in an amount sufficient to achieve therapeutic levels at the appropriate target. The release of the active agent from the first drug compartment will likely occur after the dissolution and/or detachment of the second drug and second polymer compartments. In some instances, the release of active agent from the first drug compartment is significantly delayed by the presence of the second drug and second polymer compartments. The release profile of active agent from the first drug compartment is predominantly controlled by the first polymer compartment. The active agent contained in the first drug compartment provides the sustained release of active agent in an amount sufficient to maintain therapeutic levels at the appropriate target throughout the 24 hour period following oral administration.

Figure 2:
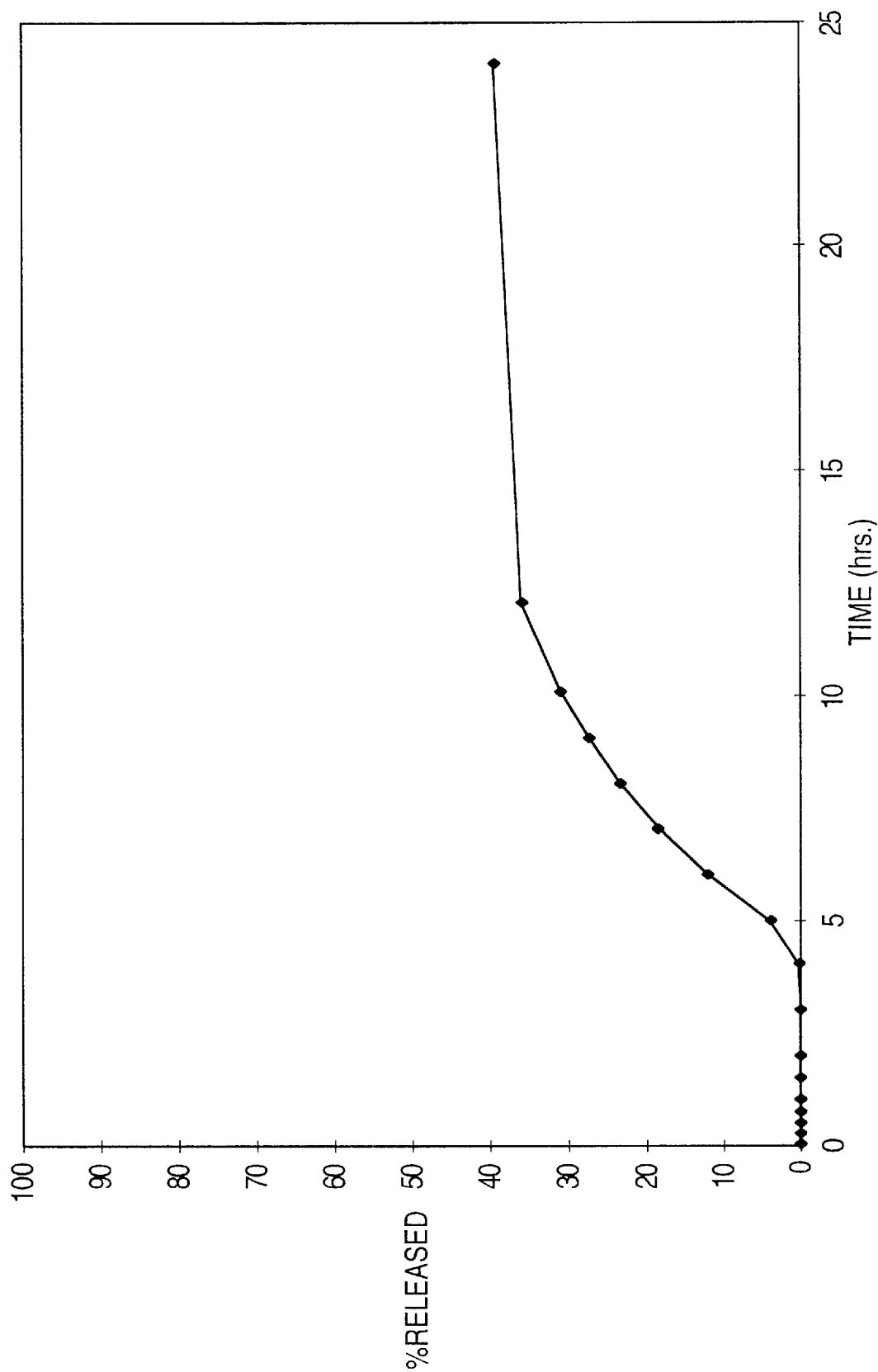

FIG. 2 is a graph showing a typical in vitro drug release profile in simulated gastric fluid (SGF) (U.S. Pharmacopeia XXIII). Due to the presence of pH sensitive polymers in the second polymer compartment, the release of active agent from the first drug compartment is significantly minimized in an acidic environment. Any release from the first drug compartment in an acidic environment would likely result only from diffusion through both the first and second polymer compartments. Although the release of active agent from second drug compartment exhibits some pH sensitivity, the ratio of pH sensitive polymers and pH independent polymers in the second polymer compartment may be adjusted so that the release of active agent from the second drug compartment is independent of pH change in the acidic range. FIG. 2 illustrates the immediate release (e.g., approximately 40% of the total dose) of active agent which occurs between 2 to 6 hours after immersion into the simulated gastric fluid. The sustained release phase did not occur throughout the 24 hour time period in simulated gastric fluid.

Figure 3:
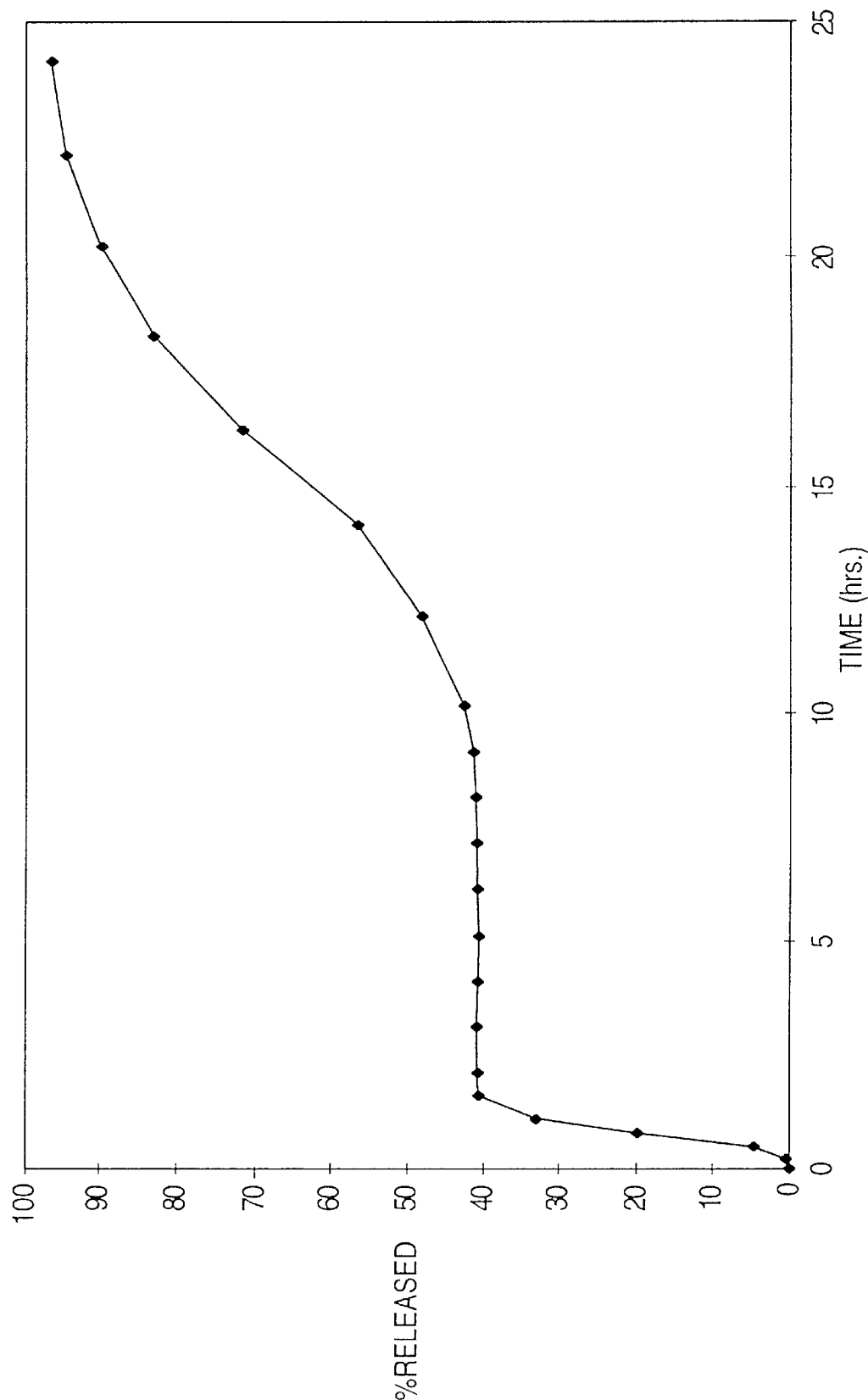

FIG. 3 is a graph showing a typical in vitro drug release profile in simulated intestinal fluid (SIF) (as described in U.S. Pharmacopeia XXIII with the exception of the absence of pancreatin). Due to the pH sensitive nature of the second polymer compartment, the release of active agent from the second drug compartment (e.g., approximately 40% of total dose) occurs almost immediately, and ends within four hours, after immersion into the simulated intestinal fluid. With the dissolution and/or detachment of the second drug and second polymer compartments, the first polymer compartment becomes exposed to the simulated intestinal fluid. The first polymer compartment predominantly controls the release of active agent from the first drug compartment. FIG. 3 further illustrates that the sustained release phase (e.g., approximately 60% of the total dose) occurs between 6 to 15 hours after immersion into the simulated intestinal fluid.

Figure 4:
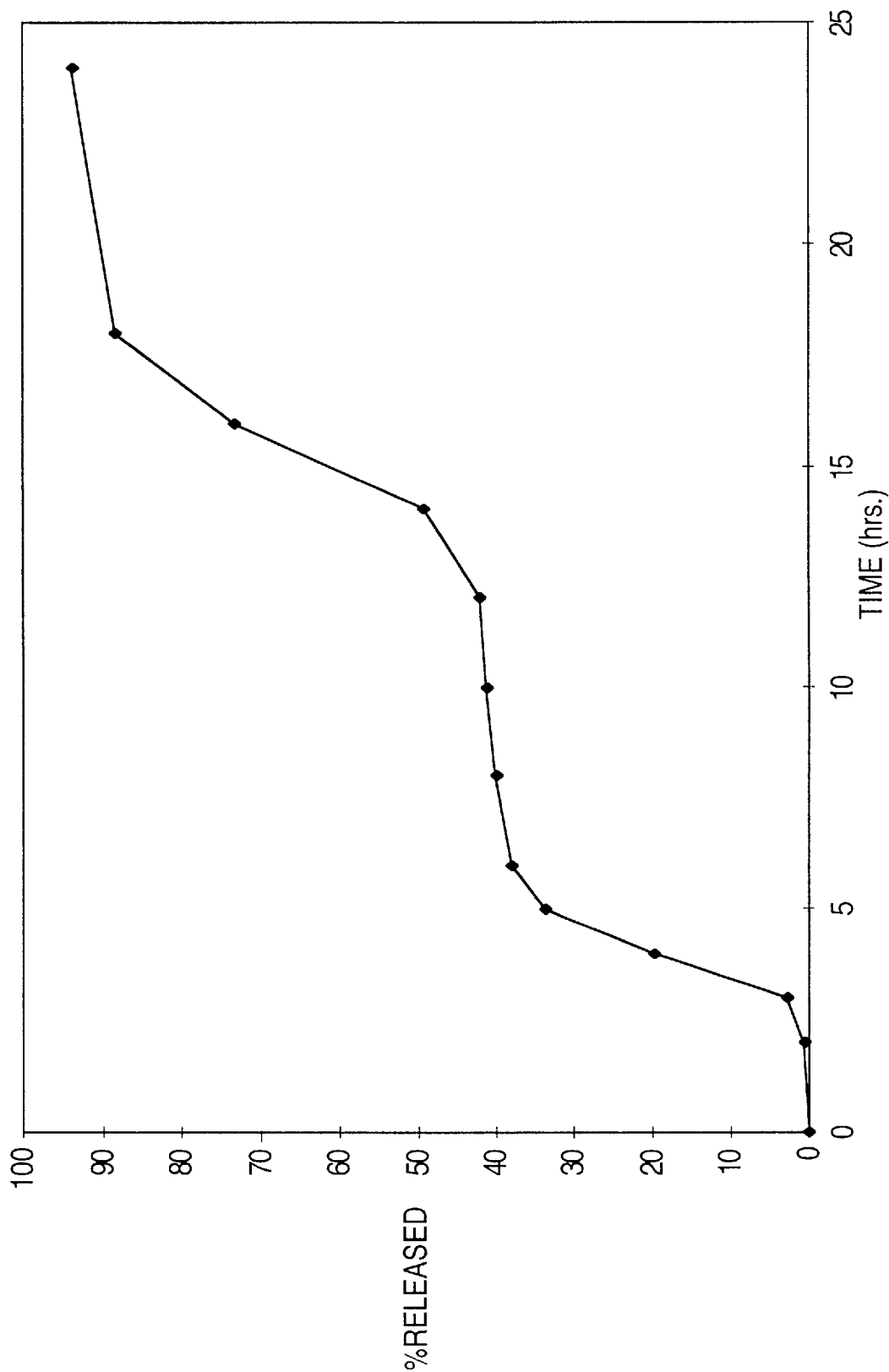

FIG. 4 is a graph showing a typical in vitro drug release profile using an apparatus 3 assembly (U.S. Pharmacopeia XXIII) with a predetermined medium pH/time program. As such, test samples may be exposed sequentially to the following media for the specified time intervals: SGF (2 hours), pH 6 (1 hour), pH 6.5 (1 hour), pH 7 (1 hour), and SIF (19 hours). A stair-step release profile is depicted in this example, with the initial release phase and the subsequent release phase directed from the second drug compartment and the first drug compartment, respectively.

DETAILED DESCRIPTION OF PREFERRED EMBODIMENTS

The present invention relates to a drug delivery system representing a single bead formulation suitable for oral administration that has multiple drug and polymer compartments which can release an active agent in multiple phases to provide an immediate yet sustained drug delivery over a 24 hour period with minimal variance between peak and trough levels.

The drug delivery system may also include a cosmetic coat compartment which substantially envelops the second polymer compartment to form a polymer/cosmetic coat interface. A cosmetic coat compartment can provide the drug delivery system with a desired glossy appearance or color.

In another embodiment, the drug delivery system also has one or more seal coat compartments. This seal coat compartment can exist at various locations of the drug delivery system, including the respective drug/polymer interfaces, the polymer/cosmetic coat interface, and substantially enveloping the second polymer compartment. In addition, a seal coat compartment may occur at multiple locations in the same drug delivery system. A seal coat compartment located at the first and third drug/polymer interfaces can minimize the solvent penetration or migration into the respective drug compartments during the coating process. A seal coat compartment located at the second drug/polymer interface or substantially enveloping the second polymer compartment can minimize the destruction or dissolution of the respective polymer compartments during production.

In one other embodiment, the first drug compartment substantially envelops a inert core. The inert core, typically a starch or sugar sphere, is a manufacturing alternative. In the pharmaceutical arts, well-known "drug layering" techniques exist to bind active agent on to the inert core (i.e., carrier) with an appropriate binding agent. The inert core typically has a diameter ranging from approximately 18 to 45 mesh and preferably within 35 to 40 mesh, if a high drug load is desired. The active agent may be layered on to the inert core using a conventional coating pan, a fluidized particle coater, or a rotogranulator.

In embodiments where an inert core is not employed, the first drug compartment may be prepared by incorporating suitable ingredients such as microcrystalline cellulose and the appropriate binders so that the active agent can be wet granulated, extruded, and spherinized to form spherical beads as described in the art.

The final single bead formulations may be filled into hard gelatin capsules to the desired weight to facilitate delivery of sufficient quantities of active agent to achieve or maintain therapeutic levels at the proper target. Final single bead formulations may also be applied to soft gelatin capsules or tablet dosage forms with the addition of proper excipients. For pediatric applications, the beads may be dispersed into a suitable liquid prior to administration.

The active agent of the present invention includes drugs that are subject to the first pass effect, and their pharmaceutically acceptable salts, pro-drug forms, metabolites, and derivatives. Various examples of such drugs include acetaminophen, aldosterone, alprenolol, amitryptyline, aspirin, beclomethasone diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropropoxyphene, dihydroergotamine, diltiazem HCl, dobutamine HCl, domperidone, dopamine HCl, doxepin HCl, epinephrine, ergoloid mesylates, ergotamine tartrate, estradiol, ethinylestradiol, flunisolide, fluorouracil, flurazepam HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, lorcainide, meperidine HCl, 6-mercaptopurine, metaproterenol sulfate, methoxamine HCl, methylphenidate, methylprednisolone, methyltestosterone mesylate, metoclopramide, metoprolol tartrate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, oxyphenbutazone, penicillamine, pentazocine HCl, pentazocine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicylamide, salbutamol, secobarbital, testosterone, terbutaline, timolol maleate, tolbutamide, and verapamil HCl.

In a preferred embodiment of the present invention, the active agent is diltiazem, or a pharmaceutically acceptable salt, diltiazem HCl. A further preferred embodiment is a drug delivery system containing diltiazem, which exhibits the following in vitro dissolution profile when measured in a type 2 dissolution apparatus (paddle method) according to U.S. Pharmacopeia XXIII at 37° C. in simulated gastric fluid at 100 rpm: (a) from about 0% to about 40% of total diltiazem is released after 3 hours of measurement in said apparatus; (b) from about 10% to about 50% of total diltiazem is released after 6 hours of measurement in said apparatus; (c) and no more than about 60% of total diltiazem is released after 12 hours of measurement in said apparatus.

In another preferred embodiment, the diltiazem exhibits the following in vitro dissolution profile when measured in a type 2 dissolution apparatus (paddle) according to U.S. Pharmacopeia XXIII at 37° C. in simulated intestinal fluid at 100 rpm: (a) from about 20% to about 50% of total diltiazem is released after 3 hours of measurement in said apparatus; (b) from about 20% to about 60% of total diltiazem is released after 6 hours of measurement in said apparatus; (c) from about 35% to about 100% of total diltiazem is released after 12 hours of measurement in said apparatus; (d) no less than about 70% of total diltiazem is released after 24 hours of measurement in said apparatus.

In yet another preferred embodiment is a drug delivery system containing diltiazem, which exhibits the following in vitro dissolution profile when measured in a type 2 dissolution apparatus (paddle) according to U.S. Pharmacopeia XXIII at 37° C. in simulated gastric fluid at 100 rpm: (a) from about 0% to about 40% of total diltiazem is released after 3 hours of measurement in said apparatus; (b) from about 10% to about 50% of total diltiazem is released after 6 hours of measurement in said apparatus; (c) no more than about 60% of total diltiazem is released after 12 hours of measurement in said apparatus; and also exhibits the following in vitro dissolution profile when measured in a type 2 dissolution apparatus (paddle) according to U.S. Pharmacopeia XXIII at 37° C. in simulated intestinal fluid at 100 rpm: (a) from about 20% to about 50% of total diltiazem is released after 3 hours of measurement in said apparatus; (b) from about 20% to about 60% of total diltiazem is released after 6 hours of measurement in said apparatus; (c) from about 35% to about 100% of total diltiazem is released after 12 hours of measurement in said apparatus; (d) no less than about 70% of total diltiazem is released after 24 hours of measurement in said apparatus.

In one further embodiment, the amount of diltiazem contained in the first drug compartment and the amount of diltiazem contained in said second drug compartment is present in a weight/weight ratio from 4:1 to 1:4. Preferably, the amount of diltiazem contained in the first drug compartment and the amount of diltiazem contained in said second drug compartment is present in a weight/weight ratio of 3:2.

The first polymer compartment, or second polymer compartment, or both first and second polymer compartments, of the drug delivery system may contain suitable water insoluble polymers such as cellulose esters, cellulose ethers, and acrylic resins. Two examples of suitable acrylate polymer for use in the second polymer compartment are Eudragit RL™ and Eudragit RS™. With respect to the first polymer compartment, the acrylate polymers Eudragit RL™ and Eudragit RS™ are acceptable.

The first polymer compartment, or second polymer compartment, or both first and second polymer compartments, of the drug delivery system may contain suitable pH sensitive polymers such as hydroxypropyl methylcellulose phthalate, cellulose acetate phthalate, other cellulose ethers or esters, and acrylic resins. Two examples of suitable acrylate polymer for use in the second polymer compartment are Eudragit L™ and Eudragit S™. With respect to the first polymer compartment, the acrylate polymers Eudragit L™ and Eudragit S™ are acceptable.

The first polymer compartment, or second polymer compartment, or both first and second polymer compartments, of the drug delivery system may contain suitable water soluble polymers such as hydroxypropyl methylcellulose, hydroxypropyl cellulose, other cellulose ethers, polyvinyl alcohol, polyvinylpyrrolidone, polyethylene glycol, starch, and hydroxyethyl cellulose.

Other excipients which can facilitate the manufacturing operation or final film quality may be included. These excipients include plasticizer, surfactant, hydrophobic anti-tackiness material, etc.

Without further elaboration, it is believed that one skilled in the art can, using the preceding description, utilize the present invention to the fullest extent. The following examples are illustrative only, and not limiting of the remainder of the disclosure in any way whatsoever.

EXAMPLE ONE

An example of the composition of the first drug compartment is set forth in Table I.

TABLE I

| Ingredient | % w/w range | % w/w example |
|---|---|---|
| diltiazem hydrochloride | 70–100 | 90 |
| binding agent(s) | 0–30 | 9 |
| surfactant | 0–10 | 1 |

Either micronized or regular sized active raw material can be used to produce the single bead formulations. Both the aqueous and the organic solvent systems have been successfully evaluated and applied to this invention. Pharmaceutically acceptable solvents such as purified water, isopropyl alcohol, ethanol, etc., may be utilized. One or more binding agents may be incorporated to bind the active diltiazem blend onto the inert core. Examples of suitable binding agents include hydroxypropyl methylcellulose, ethyl cellulose, polyvinylpyrrolidone, polymerized acrylates, hydroxypropyl cellulose, hydroxyethyl cellulose, etc. Based upon the binding agent selected, the ratio between diltiazem and binding agent can vary widely.

The surfactant is employed, if necessary, to improve the texture of the drug compartments and/or properties of the final dosage form. Other pharmaceutical excipients such as glidant, anti-caking agent, lubricant, etc., may also be incorporated in the drug compartments to further improve the properties of the final product as described in the art.

The first polymer compartment provides approximately 6 to 12 hours lag time upon exposure to the surrounding medium before the sustained release phase of diltiazem from the first drug compartment. The polymer materials may include, but are not limited to, polymerized acrylates or copolymers of acrylic and methacrylic acid esters or esters of either monomer (hereinafter polymerized acrylates), methacrylic acid and methyl methacrylate copolymer (hereinafter methacrylic acid copolymer). These polymerized acrylates and methacrylic acid copolymers are commercially available from Rohm Tech Inc. under the tradenames Eudragit RS™, Eudragit RL™, Eudragit S™, and Eudragit L™. Other water insoluble polymers such as ethylcellulose, cellulose acetate, polydimethylsiloxane, etc., may also be employed to achieve the desired release characteristics. Water soluble polymers may also be incorporated in the polymer compartment. Examples of such polymers include, but are not limited to, hydroxypropyl methylcellulose, hydroxypropyl cellulose, polyvinylpyrrolidone, etc. Other pharmaceutically acceptable ingredients known in the art, such as water soluble pore formers, plasticizers, anti-caking (or anti-adherent) agents, lubricants, separating substances, anti-forming agents, surfactants, etc., may also be incorporated in the polymeric coating to achieve the desired properties or performance.

The first polymer compartment may be formed by various pharmaceutical coating technologies known in the art using suitable coating equipment such as pan coaters, fluidized particle coaters, and rotogranulators.

An example of the first polymer compartment composition is shown below:

TABLE II

| Ingredient | % w/w range | % w/w example |
|---|---|---|
| Eudragit RS 100 ™ | 0–45 | 28 |
| Eudragit RL 100 ™ | 0–30 | 5 |
| Eudragit S 100 ™ | 0–45 | 28 |
| Eudragit L 100 ™ | 0–30 | 5 |
| Plasticizer | 5–25 | 12 |
| anti-caking agent | 10–55 | 22 |

All the ingredients listed above may be dissolved or dispersed in the following solvent system, whether used alone or in combination: purified water, isopropyl alcohol, acetone, ethanol, etc. The weight of the dry solids applied to the first drug compartment may be in the range of about 20% to about 60% w/w, typically 40% w/w, of the total weight of the beads at this stage, i.e., the total weight of the inert core, if any, and the first drug and first polymer compartments. A sufficient quantity of the polymeric mixture is required to envelop the active core to ensure the desired lag time and release characteristics. The exact quantity may have to be adjusted carefully depending upon the formulation composition and the manufacturing processing conditions. The size of the first drug compartment dictates the bead surface area and therefore affects the thickness of the first polymer compartment if a fixed quantity of polymeric material is applied on to the first drug compartment.

The second drug compartment may consist of a similar formulation composition as that of the first drug compartment, which Table I illustrates. The ratio of diltiazem in the first drug compartment and the second drug compartment may be in the range of 4:1 w/w to 1:4 w/w, preferably 3:2 w/w.

The second polymer compartment provides 0 to 4 hours lag time upon exposure to the surrounding medium before the immediate release phase of diltiazem from the second drug compartment. The polymer materials may include, but are not limited to, polymerized acrylates or copolymers of acrylic and methacrylic acid esters or esters of either monomer (hereinafter polymerized acrylates), methacrylic acid and methyl methacrylate copolymer (hereinafter methacrylic acid copolymer). These polymerized acrylates and methacrylic acid copolymers are commercially available from Rohm Tech Inc. under the tradenames Eudragit RS™, Eudragit RL™, Eudragit S™, and Eudragit L™. Enteric polymers which dissolve in weakly acidic, neutral or slightly alkaline medium may be incorporated to ensure the breakage of the polymer coating and thus expose the first polymer compartment when the dosage form reaches small intestine and loses all the diltiazem in the second drug compartment. Other water insoluble polymers such as ethylcellulose, cellulose acetate, polydimethylsiloxane, etc., may also be employed to achieve the desired release characteristics. Water soluble polymers may also be incorporated in the polymer coat. Examples of such polymers include, but are not limited to, hydroxypropyl methylcellulose, hydroxypropyl cellulose, hydroxyethyl cellulose, polyvinylpyrrolidone, etc. Other pharmaceutically acceptable ingredients known in the art, such as water soluble pore formers, plasticizers, anti-caking (or anti-adherent) agents, lubricants, separating substances, anti-forming agents, etc., may also be incorporated in the polymeric coating to achieve the desired properties or performance.

The second polymer compartment may be formed by various pharmaceutical coating technologies known in the art using suitable coating equipment such as pan coaters, fluidized particle coaters, and rotogranulators.

An example of the second polymer compartment composition is shown below:

TABLE III

| Ingredient | % w/w range | % w/w example |
|---|---|---|
| Eudragit RS 100 ™ | 0–30 | 10 |
| Eudragit L 100 ™ | 0–50 | 30 |
| Plasticizer | 5–25 | 10 |
| anti-caking agent | 10–65 | 50 |

All the ingredients listed above may be dissolved or dispersed in the following solvent system, whether used alone or in combination: purified water, isopropyl alcohol, acetone, ethanol, etc. The weight of the dry solids applied to the second drug compartment core may be in the range of about 5% to about 30% w/w, typically 16% w/w, of the total weight of the beads at this stage, i.e., the total weight of the inert core, if any, the first drug and first polymer compartments, and the second drug and second polymer compartments.

An example of the in vitro dissolution profile of the drug delivery system containing diltiazem described above in a type 2 dissolution apparatus (paddle) according to U.S. Pharmacopeia XXIII at 37° C. in 0.1N HCl at 100 rpm is shown below:

TABLE IV

| Hours | % Released (Preferred Range) |
|---|---|
| 3 | 0–40 |
| 6 | 0–50 |
| 24 | 25–60 |

An example of the in vitro dissolution profile of the drug delivery system containing diltiazem described above in a type 2 dissolution apparatus (paddle) according to U.S. Pharmacopeia XXIII at 37° C. in simulated gastric fluid (SGF) at 100 rpm is shown below:

TABLE V

| Hours | % Released (Preferred Range) |
|---|---|
| 3 | 0–40 |
| 6 | 0–50 |
| 24 | 25–60 |

An example of the in vitro dissolution profile of the drug delivery system containing diltiazem described above in a type 2 dissolution apparatus (paddle) according to U.S. Pharmacopeia XXIII at 37° C. in simulated intestinal fluid (SIF) at 100 rpm is shown below:

TABLE VI

| Hours | % Released (Preferred Range) |
|---|---|
| 3 | 20–50 |
| 6 | 20–60 |
| 12 | 35–100 |
| 24 | 70–100 |

An example of the in vitro dissolution profile of the drug delivery system containing diltiazem described above in a type 3 bio-disk method according to U.S. Pharmacopeia XXIII at 37° C. in a predetermined pH/time program at 100 rpm is shown below. An example of the predetermined pH/time program is as follows: SGF-2 hours; pH 6-1 hour; pH 6.5-1 hour; pH 7-1 hour; and SIF-19 hours.

TABLE VII

| Hours | % Released (Preferred Range) |
|---|---|
| 3 | 0–40 |
| 6 | 20–60 |
| 12 | 30–100 |
| 24 | 80–100 |

Those skilled in the art will find it apparent that various modifications and variations can be made to the formulations of this invention. Thus, the present invention is intended to cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A single bead drug delivery system suitable for oral administration comprising:
    a) a first drug compartment containing an effective amount of an active agent, or a pharmaceutically acceptable salt thereof, optionally in association with a pharmaceutically acceptable binder or excipient;
    b) a first polymer compartment which substantially envelops said first drug compartment to form a first drug/polymer interface;
    c) a second drug compartment containing an effective amount of an active agent, or a pharmaceutically acceptable salt thereof, optionally in association with a pharmaceutically acceptable binder or excipient, wherein said second drug compartment substantially envelops said first polymer compartment to form a second drug/polymer interface;
    d) a second polymer compartment which substantially envelops said second drug compartment to form a third drug/polymer interface; and
    wherein said single bead drug delivery system can release said active agent in multiple phases.

2. The drug delivery system of claim 1, which further comprises:
    e) a cosmetic coat compartment which substantially envelops said second polymer compartment to form a polymer/cosmetic coat interface.

3. The drug delivery system of claim 1, which further comprises a seal coat compartment at said first drug/polymer interface.

4. The drug delivery system of claim 1, which further comprises a seal coat compartment at said second drug/polymer interface.

5. The drug delivery system of claim 1, which further comprises a seal coat compartment at said third drug/polymer interface.

6. The drug delivery system of claim 1, which further comprises a seal coat compartment that substantially envelops said second polymer compartment.

7. The drug delivery system of claim 2, which further comprises a seal coat compartment at said polymer/cosmetic coat interface.

8. The drug delivery system of claim 1, which further comprises a first seal coat compartment at said first drug/polymer interface and a second seal coat compartment at said third drug/polymer interface.

9. The drug delivery system of claim 1, which further comprises a first seal coat compartment at said second drug/polymer interface and a second seal coat compartment that substantially envelops said second polymer compartment.

10. The drug delivery system of claim 2, which further comprises a first seal coat compartment at said second drug/polymer interface and a second seal coat compartment at said polymer/cosmetic coat interface.

11. The drug delivery system of claim 1, wherein said first drug compartment substantially envelops an inert core.

12. The drug delivery system of claim 1, wherein said active agent is diltiazem, or a pharmaceutically acceptable salt thereof.

13. The drug delivery system of claim 12, wherein said diltiazem exhibits the following in vitro dissolution profile when measured in a type 2 dissolution apparatus (paddle) according to U.S. Pharmacopeia XXIII at 37° C. in simulated gastric fluid at 100 rpm:
 a) from about 0% to about 40% of total diltiazem is released after 3 hours of measurement in said apparatus;
 b) from about 10% to about 50% of total diltiazem is released after 6 hours of measurement in said apparatus; and
 c) no more than about 60% of total diltiazem is released after 12 hours of measurement in said apparatus.

14. The drug delivery system of claim 12, wherein said diltiazem exhibits the following in vitro dissolution profile when measured in a type 2 dissolution apparatus (paddle) according to U.S. Pharmacopeia XXIII at 37° C. in simulated intestinal fluid at 100 rpm:
 a) from about 20% to about 50% of total diltiazem is released after 3 hours of measurement in said apparatus;
 b) from about 20% to about 60% of total diltiazem is released after 6 hours of measurement in said apparatus;
 c) from about 35% to about 100% of total diltiazem is released after 12 hours of measurement in said apparatus; and
 d) no less than about 70% of total diltiazem is released after 24 hours of measurement in said apparatus.

15. The drug delivery system of claim 12, wherein said diltiazem exhibits the following in vitro dissolution profile when measured in a type 2 dissolution apparatus (paddle) according to U.S. Pharmacopeia XXIII at 37° C. in simulated gastric fluid at 100 rpm:
 a) from about 0% to about 40% of total diltiazem is released after 3 hours of measurement in said apparatus;
 b) from about 10% to about 50% of total diltiazem is released after 6 hours of measurement in said apparatus; and
 c) no more than about 60% of total diltiazem is released after 12 hours of measurement in said apparatus; and
wherein said diltiazem exhibits the following in vitro dissolution profile when measured in a type 2 dissolution apparatus (paddle) according to U.S. Pharmacopeia XXIII at 37° C. in simulated intestinal fluid at 100 rpm:
 a) from about 20% to about 50% of total diltiazem is released after 3 hours of measurement in said apparatus;
 b) from about 20% to about 60% of total diltiazem is released after 6 hours of measurement in said apparatus;
 c) from about 35% to about 100% of total diltiazem is released after 12 hours of measurement in said apparatus; and
 d) no less than about 70% of total diltiazem is released after 24 hours of measurement in said apparatus.

16. The drug delivery system of claim 12, wherein the amount of diltiazem contained in said first drug compartment and the amount of diltiazem contained in said second drug compartment is present in a weight/weight ratio from 4:1 to 1:4.

17. The drug delivery system of claim 12, wherein the amount of diltiazem contained in said first drug compartment and the amount of diltiazem contained in said second drug compartment is present in a weight/weight ratio of 3:2.

18. The drug delivery system of claim 1, wherein said first polymer compartment, or second polymer compartment, or both first and second polymer compartments, contains one or more water insoluble polymer(s) selected from the group consisting of cellulose esters, cellulose ethers, and acrylic resins.

19. The drug delivery system of claim 1, wherein said first polymer compartment, or second polymer compartment, or both first and second polymer compartments, contains one or more pH sensitive polymer(s) selected from the group consisting of hydroxypropyl methylcellulose phthalate, cellulose acetate phthalate, other cellulose ethers or esters, and acrylic resins.

20. The drug delivery system of claim 1, wherein said first polymer compartment, or second polymer compartment, or both first and second polymer compartments, contains one or more water soluble polymer(s) selected from the group consisting of hydroxypropyl methylcellulose, hydroxypropyl cellulose, other cellulose ethers, polyvinyl alcohol, polyvinylpyrrolidone, polyethylene glycol, starch, and hydroxyethyl cellulose.

* * * * *